United States Patent [19]

Daly et al.

[11] 4,177,620
[45] Dec. 11, 1979

[54] METHOD OF FORMING A STERILIZABLE PACKAGE WITH TEAR-OFF INDICATORS

[75] Inventors: William P. Daly, White Plains, N.Y.; Robert P. Lewis, Oceanport; Oliver L. Pouliot, Oradell, both of N.J.

[73] Assignee: Faser Industries, Saddle Brook, N.J.

[21] Appl. No.: 904,671

[22] Filed: May 10, 1978

Related U.S. Application Data

[62] Division of Ser. No. 780,399, Mar. 23, 1977, Pat. No. 4,121,714.

[51] Int. Cl.² .............................................. B65B 55/02
[52] U.S. Cl. ..................................................... 53/425
[58] Field of Search .................. 53/425, 426; 206/363, 206/439, 459

[56] References Cited

U.S. PATENT DOCUMENTS

| 3,815,315 | 6/1974 | Glick | 53/425 |
| 4,091,921 | 5/1978 | Lewis | 206/459 X |

Primary Examiner—Travis S. McGehee
Attorney, Agent, or Firm—Sprung, Felfe, Horn, Lynch & Kramer

[57] ABSTRACT

A sterilizable package or pouch is made from a plastic member, generally transparent, which is marginally heat sealed around three sides to a paper member so as to leave an opening at one end for inserting the package contents. The paper member has a portion which extends beyond the area to be enclosed by the marginal heat seal when completed. This portion bears indicia, generally printed on the paper, that changes color upon sterilization (either steam or gas sterilization). The indicia bearing portion is adapted to be separated from the package and inserted therein together with the package contents before the marginal heat seal is completed and the package contents are sterilized.

2 Claims, 4 Drawing Figures

METHOD OF FORMING A STERILIZABLE PACKAGE WITH TEAR-OFF INDICATORS

This is a division of application Ser. No. 780,399, filed Mar. 23, 1977, now U.S. Pat. No. 4,121,714.

BACKGROUND

This invention relates to a sterilizable package or pouch made of a plastic member heat sealed to a paper member wherein the paper member is provided with a portion which can be separated from the package which carries indicia that changes color upon sterilization.

Such packages are made by marginally heat sealing a clear plastic laminate to surgical grade kraft paper or the like and have come into widespread use. The paper portion of such packages is designed to be sufficiently porous to permit gas or steam sterilization but is otherwise impervious to bacteria. The plastic laminate is heat sealable to the paper, stable under sterilization conditions, impervious to bacteria and permits visual identification of the package contents.

Such packages are used for medical implements that must be sterile prior to use. The manufacturer or user, such as a hospital or clinic, of such medical implements is supplied with a package heat sealed around three sides by the package manufacturer. The medical implement is then placed in the package and the fourth side is heat sealed to complete the marginal heat seal between the paper and the plastic. The package contents are then sterilized, either by exposure to ethylene oxide gas or by steam autoclaving and the package and its sterile contents can be stored for indefinite periods of time in a sterile condition.

To determine if a sealed package has been subjected to sterilization, it has been common practice to employ indicator inks that change color upon gas or steam sterilization and these indicator inks are typically printed on the exterior and/or interior of the paper member of the sterilizable package (cf U.S. Pat. Nos. 3,093,242 to Huyck et al and 3,991,881 to Augurt). There are drawbacks to printing such indicator inks on the paper member in the area forming the heat sealed enclosure for the package contents with the plastic member. The main difficulty with indicator inks printed on either side of the paper member is that the package may be subjected to sterilization conditions which are sufficient to cause a color change in the indicator ink but insufficient to actually sterilize the package contents. With an indicator ink printed on the outside of the paper member the color change will occur as soon as the indicator ink comes in contact with steam or ethylene oxide gas and long before either gas penetrates the paper member and sterilizes the package contents. Printing the indicator ink on the inside of the paper member is an improvement but again, the ethylene oxide gas or steam in passing through the paper member comes in contact with the indicator ink before reaching the package contents. To cope with these problems, manufacturers and hospitals have to follow sterilization procedures with a built-in margin of safety to ensure that the package contents are sterilized which means using high sterilization temperatures over a sustained period of time. Because of these drawbacks, the indicator inks printed on the inside or the outside of the paper member simply say that the package has been put through sterilization but it is left up to the technician to ensure that the correct sterilization procedure has been observed to effectively sterilize the package contents.

SUMMARY

The present invention overcomes these and other drawbacks by providing a member having the desired indicator ink printed thereon which is inserted into the package together with the implement to be sterilized prior to completing the marginal heat seal and subjecting the package to sterilization. The indicia bearing member is provided by printing the indicator inks on a portion of the paper member of the package which extends beyond the area enclosed by the marginal heat seal and making it readily separable from the package. The indicia bearing portion, inserted with the item or implement to be sterilized in the package, can be positioned and oriented such that the indicator ink faces the plastic member of the package which means that the sterilization gas will act on the indicator ink to cause the color change at the same time or after sterilization of the package contents has been accomplished. This provides a much better indication to the ultimate user of the sterile item that it is, in fact, in a sterile condition and not simply that the package has gone through a sterilization procedure.

The sterilizable package of the invention includes a plastic member marginally heat sealed around three sides to a paper member so as to leave an opening at one end for inserting the package contents. The paper member has a portion which extends beyond the area to be enclosed by the marginal heat seal when completed and this portion of the paper member bears indicia (for example indicator inks as commonly employed in the art) that change color upon sterilization. The indicia bearing portion is adapted to be separated or severed from the package and inserted therein together with the package contents prior to completing the marginal heat seal and sterilization of the package contents.

The present invention also provides a method for sterilizing which includes providing an open-ended package made of a plastic member heat sealed to a paper member wherein the paper member has a portion extending beyond the area to be enclosed by the heat seal when completed, said portion bearing indicia that changes color upon sterilization, inserting the item or implement to be sterilized into the open-ended package, separating the indicia bearing portion from the package and inserting said separating portion into the package with the indicia visible through the plastic member, heat sealing the open end of the package and subjecting the sealed package to sterilization. Preferably the indicia bearing portion is positioned between the item to be sterilized and the plastic member with the indicia visible through the plastic member. This, of course, depends on the nature and the size of the item or implement to be sterilized.

DESCRIPTION OF THE DRAWING

The present invention will be more fully understood from the following description taken in conjunction with the accompanying drawing wherein.

DESCRIPTION

Figure 2:
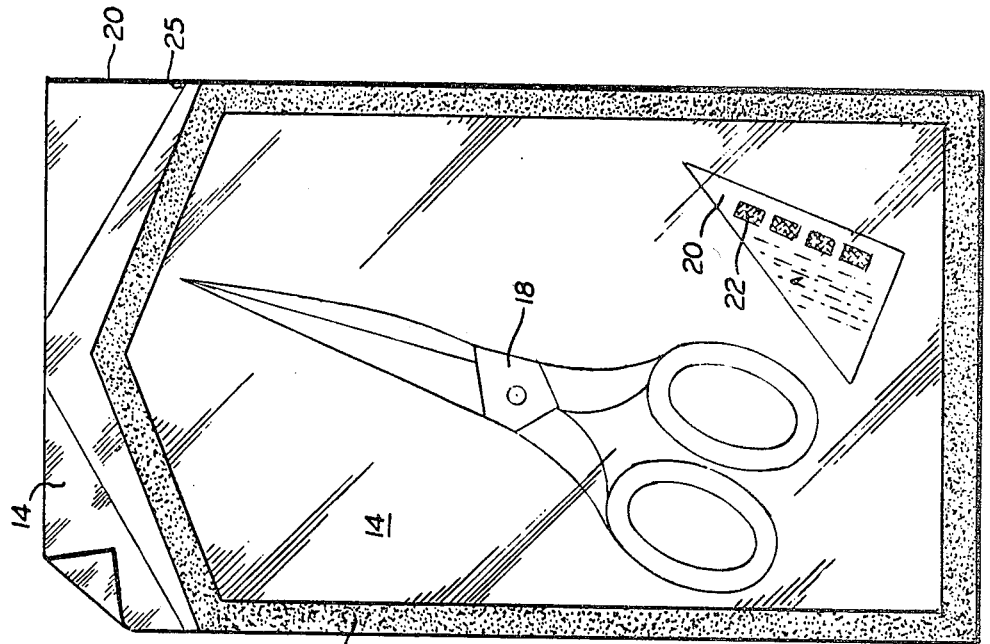
FIG. 2 is a top plan view of the sterilization pouch of FIG. 1 from the plastic side showing the marginal heat seal completed and one of the triangular shaped indicia bearing portions separated from the package and inserted into the package interior with the package contents with the indicia visible through the plastic member.
Figure 1:
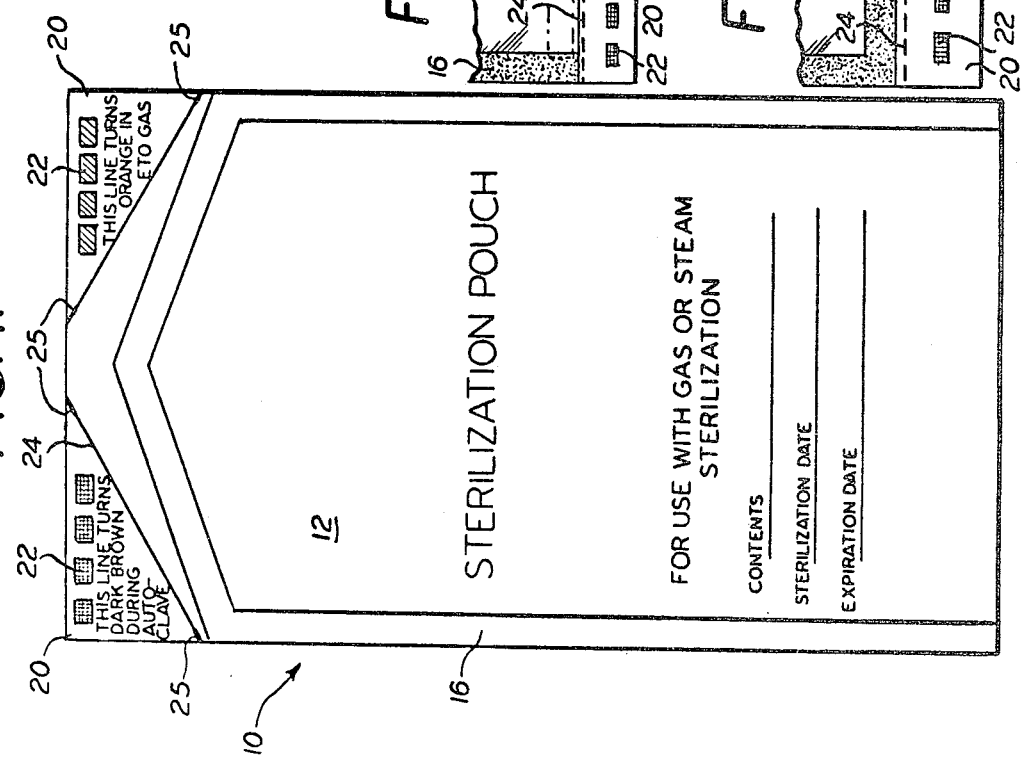
FIG. 1 is a top plan view of a preferred sterilizable pouch according to the invention from the paper side and having triangular tear-off indicator portions.

Referring now to the drawing FIGS. 1 and 2 thereof the sterilizable pouch of the invention is shown generally by reference numeral 10 and includes a paper member 12 marginally heat sealed at 16 around three sides (FIG. 1) to a plastic member 14 so as to leave an opening at one end for inserting the package contents. The paper member 12, in the preferred embodiment shown in FIGS. 1 and 2 has triangular shaped portions 20 extending beyond an inverted V-end seal which is beyond the area to be enclosed by the marginal heat seal 16 when completed (FIG. 2). As shown in FIG. 1, the portions 20 bear indicia that changes color upon sterilization, one portion bearing indicia that changes color upon steam sterilization and the other portion 20 indicia that changes color upon gas sterilization such as ethylene oxide gas. The indicia which is commonly referred to as indicator inks is generally shown by the reference numeral 22.

Suitable indicator inks for the indicia 22 are any of the commerically available and commonly used indicator inks for sterilization pouches. A typical indicator ink for use with steam autoclaving is a chemically active ink that changes from pink to dark brown during steam autoclaving. A typical indicator ink for use with ethylene oxide sterilization is a chemically active ink that changes color from light brown or tan to orange upon exposure to ethylene oxide gas sterilization.

Steam autoclaving and ethylene oxide gas are known sterilization techniques and the present invention is well adapted to these procedures.

An item to be sterilized such as the scissors 18 shown in FIG. 2 is inserted through the open end of the pouch shown in FIG. 1. Depending on the sterilization procedure to be employed, the technician separates the proper indicia bearing portion 20 each of which is attached to the paper portion 12 at 25 and precut therebetween along line 25. The technician or operator then inserts the separated portion 20 into the package with the indicia 22 visible through the plastic member 14 as shown in FIG. 2. The marginal heat seal 16 is then completed and the package is ready for sterilization.

During sterilization, the sterilizing medium, steam or ethylene oxide gas, sterilizes the scissors 18 and at the same time or afterwards, reaches the indicia 22 which then undergoes the indicated color change to indicate that the package contents and not just the package itself are sterile. Depending on the nature and size of the item or implement to be sterilized, it is preferred to position the portion 20 which is inserted into the pouch between the item to be sterilized and the plastic member which ensures that the sterilization medium will not cause a color change in the color sensitive indicia until after the sterilizing medium has contacted the item to be sterilized. In any event, the indicia 20 must be visible through the plastic member 14 when the portion 20 is separated from the package 10 and inserted into the interior thereof with the item to be sterilized.

The preferred embodiment shown in FIGS. 1 and 2 has a further advantage in that sealed packages ready for sterilization can be segregated by the intended sterilization procedure to be employed by virtue of the fact that one of the indicia-bearing portions 20 is missing from either the left or right side of each sealed pouch when the pouches are lined up and oriented in the same direction. Thus, it is easy to detect if a package designated for steam sterilization has become mixed in with packages designated for ethylene oxide sterilization.

Figure 3:
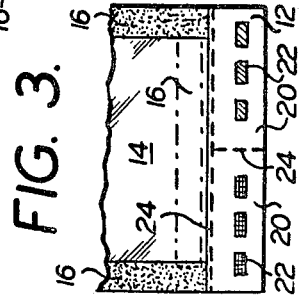
FIG. 3 is a top plan view partly broken away of an alternate embodiment of the present invention of a sterilization pouch from the plastic side.
Figure 4:
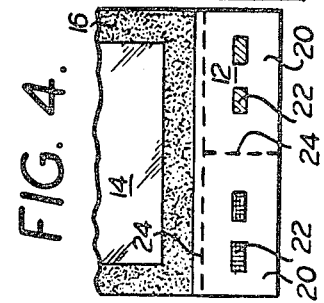
FIG. 4 is a top plan view, partly broken away, of a further embodiment of a sterilization pouch of the invention also from the plastic side thereof.

FIGS. 3 and 4 show alternate embodiments of the present invention. In FIG. 3, the indicia bearing portions 20 are defined via perforated lines 24 at the bottom or open end of the sterilization pouch. After the item to be sterilized is inserted into the pouch under plastic member 14, the desired portion 20 of the paper member 12 is separated and inserted into the pouch with the item to be sterilized with the indicia 22 visible through the plastic member 14. The transverse heat seal across the bottom shown by dash lines is then made to complete the marginal heat seal 16.

The embodiment shown in FIG. 4 is similar to the embodiment shown in FIG. 1 except the end seal opposite the open end of the pouch is a straight transverse seal and the portion of the paper member 12 extending beyond the area to be enclosed by the marginal heat seal 16 is divided into two rectangular indicia bearing portions 20 via perforated line 24.

The sterilization pouch of the invention will typically bear other indicia as shown in FIG. 1, for example, on the exterior side of the paper member 12 to designate for example the package contents, the sterilization date, the expiration date and the like.

Paper member 12 can be made from commercially available surgical grade kraft paper having the desired porosity characteristics. The color sensitive indicia 22 is commonly printed on the paper member 12 using known techniques. The terms "paper" as used herein also applies to synthetic or artificial paper materials made from plastic fibers and the like, as well as two conventional paper products having the necessary characteristics for use in sterilization pouches. An example of synthetic paper used for such pouches is a spun bonded polyethylene sold by DuPont under the trademark "TYVEK".

The plastic member 14 is preferably a laminate of a polyester such as polyethylene ateraphthalate sold under the trademark "MYLAR", and a heat sealable thermoplastic material such as ployethylene, polypropylene, ethylene vinyl acetate, an ionomer such as DuPont's "SURLYN", copolymers and mixtures of the foregoing. The polyester layer forms the exterior side of the package and the heat sealable thermoplastic material interfaces with the paper member 12 for forming the marginal heat seal 16.

Forming the marginal heat seal 16 between the paper member 12 and the plastic member 14 as shown in FIGS. 1 and 2 can be accomplished using conventional heat sealing techniques and equipment. Generally the heat seal is made wide enough to guarantee an adequate and complete seal around the margin of the package which is initially formed with a heat seal around three sides with the fourth side being completed after the package contents are inserted therein as shown in FIG. 2. If desired, a number of parallel spaced apart seals can be effected in the area of the marginal heat seal 16. This is commonly known in the industry as a rib seal and is employed to impart additional peel strength to the heat seal between the plastic member 14 and the paper member 12.

What is claimed is:

1. Method for sterilizing which comprises providing an open-ended package made of a plastic member heat sealed to a paper member, the paper member having a portion extending beyond the area to be enclosed by the heat seal when completed, said portion bearing indicia that changes color upon sterilization, inserting the item to be sterilized into the open-ended package, separating the indicia bearing portion from the package and inserting said separated portion into the package with the indicia visible through the plastic member, heat sealing the open end of the package and subjecting the sealed package to sterilization.

2. Method of claim 1 wherein the indicia bearing portion is positioned between the item to be sterilized and the plastic member with the indicia visible through the plastic member.